US010314253B2

(12) United States Patent
Abdel-Haleem et al.

(10) Patent No.: US 10,314,253 B2
(45) Date of Patent: *Jun. 11, 2019

(54) METHODS AND COMPOSITIONS FOR WATERMELON SEX EXPRESSION

(71) Applicant: SEMINIS VEGETABLE SEEDS, INC., St. Louis, MO (US)

(72) Inventors: Hussein Abdel-Haleem, Athens, GA (US); Steven Knapp, Woodland, CA (US); Cecilia McGregor, Athens, GA (US); Jason Prothro, Thomasville, GA (US)

(73) Assignee: SEMINIS VEGETABLE SEEDS, INC., Woodland, CA (US)

( * ) Notice: Subject to any disclaimer, the term of this patent is extended or adjusted under 35 U.S.C. 154(b) by 865 days.

This patent is subject to a terminal disclaimer.

(21) Appl. No.: 14/094,700

(22) Filed: Dec. 2, 2013

(65) Prior Publication Data
US 2014/0157450 A1 Jun. 5, 2014

Related U.S. Application Data

(60) Provisional application No. 61/733,344, filed on Dec. 4, 2012.

(51) Int. Cl.
*A01H 1/04* (2006.01)
*A01H 5/08* (2018.01)
*C12N 15/82* (2006.01)

(52) U.S. Cl.
CPC .............. *A01H 5/08* (2013.01); *A01H 1/04* (2013.01); *C12N 15/827* (2013.01)

(58) Field of Classification Search
CPC ..................................................... A01H 5/08
See application file for complete search history.

(56) References Cited

U.S. PATENT DOCUMENTS

| | | | |
|---|---|---|---|
| 5,866,764 A | 2/1999 | Gabor et al. | |
| 6,096,944 A | 8/2000 | Vierling et al. | |
| 6,207,367 B1 | 3/2001 | Helentjaris et al. | |
| 6,399,855 B1 | 6/2002 | Beavis | |
| 6,414,226 B1 | 7/2002 | Hoogstraten | |
| 6,639,132 B1 | 10/2003 | Duvick et al. | |
| 6,670,530 B2 | 12/2003 | Eby et al. | |
| 2003/0172412 A1 | 9/2003 | Zhang et al. | |
| 2005/0015827 A1 | 1/2005 | Podlich et al. | |
| 2005/0204780 A1 | 9/2005 | Moridaira et al. | |
| 2005/0216545 A1 | 9/2005 | Aldrich et al. | |
| 2005/0218305 A1 | 10/2005 | Tsukamoto et al. | |
| 2006/0005284 A1 | 1/2006 | Tolla et al. | |
| 2009/0031438 A1 | 1/2009 | Kennard et al. | |
| 2009/0136938 A1 | 5/2009 | Tao et al. | |
| 2010/0306883 A1 | 12/2010 | Tolla et al. | |
| 2014/0041078 A1* | 2/2014 | Bachlava | A01H 5/08 800/267 |

FOREIGN PATENT DOCUMENTS

| | | |
|---|---|---|
| WO | WO 2000/070933 | 11/2000 |
| WO | 2003/051103 | 6/2003 |
| WO | 2003/096798 | 11/2003 |
| WO | WO 2012/069539 | 5/2012 |
| WO | 2014/025768 A1 † | 2/2014 |

OTHER PUBLICATIONS

Sandlin (Genetic Mapping in Citrullus lanatus, Thesis, University of Georgia, Dec. 2010).*
Prothro (Genetic mapping of phenotypic and quantitative trait loci underlying horticulturally important traits in watermelon, Thesis, University of Georgia, Dec. 2010).*
Mauricio, R. Mapping quantitative trait loci in plants: uses and caveats for evolutionary biology. Nature Reviews Genetics 2, 370-381 (2001) (Year: 2001).*
Sandlin (Genetic Mapping in Citrullus lanatus, Thesis, University of Georgia, Dec. 2010) (Year: 2010).*
Abdelmohsin et al., "Pleiotropic effect of sex expression on fruit shape in melon," In: Pitrat, M. (ed.), Cucurbitaceae 2008, Proceedings of the IXth EUCARPIA Meeting on Genetics and Breeding of Cucurbitaceae, Avignon, France, pp. 551-555, 2008.
Boualem et al., "A conserved ethylene biosynthesis enzyme leads to andromonoecy in two cucumis species," *PLoS ONE* 4(7):e6144, 2009.
Boualem et al., "A conserved mutation in an ethylene biosynthesis enzyme leads to andromonoecy in melons," *Science* 321:836-838, 2008.
Churchill et al., "Empirical threshold values for quantitative trait mapping," *Genetics* 138(3):963-971, 1994.
Doerge et al., "Permutation tests for multiple loci affecting a quantitative character," *Genetics* 142(1):285-294, 1996.
European Search Report (partial) issued in European Application No. 13195763.1, dated Feb. 20, 2014.
Fernandez-Silva et al., "Shaping melons: agronomic and genetic characterization of QTLs that modify melon fruit morphology," *Theor. Appl. Genet.* 121(5):931-940, 2010.
Ferreira et al., "Sexual expression and mating system in watermelon: Implications for breeding programs," *Crop Breeding and Appl. Biotechnol.* 2:39-48, 2002.
Grumet et al., "Sex Expression in Cucurbits," in: Wang, Y.-H., Behera, T. K., and Kole, C. (eds.) *Genetics, Genomics and Breeding of Cucurbits.* Science Publishers. Enfield, New Hampshire, pp. 353-375, 2011.
Knopf et al., "The female-specific Cs-ACS1G gene of cucumber. A case of gene duplication and recombination between the non-sex-specific 1-aminocyclopropane-1-carboxylate synthase gene and a branched-chain amino acid transaminase gene," *Plant Cell Physiol.* 47:1217-1228, 2006.

(Continued)

Primary Examiner — Lee A Visone
(74) Attorney, Agent, or Firm — Dentons US LLP; Alissa Eagle

(57) ABSTRACT

The present disclosure provides for unique watermelon plants with a desired sex expression phenotype and their progeny. Such plants may comprise an introgressed QTL associated with a desired sex expression phenotype. In certain aspects, compositions, including distinct polymorphic molecular markers, and methods for producing, breeding, identifying, selecting, and the like of plants or germplasm with a desired sex expression phenotype are provided.

19 Claims, 3 Drawing Sheets

Specification includes a Sequence Listing.

(56) References Cited

OTHER PUBLICATIONS

Li et al., "Molecular Isolation of the M Gene Suggests That a Conserved-Residue Conversion Induces the Formation of Bisexual Flowers in Cucumber Plants," *Genetics* 182:1381-1385, 2009.

Loy, "Fruit Size in Melon in Monoecious and Andromonoecious Isolines," *Cucurbit Genetics Cooperative Report* 28-29:12-13, 2005-2006.

Martin et al., "A transposon-induced epigenetic change leads to sex determination in melon," *Nature* 461:1135-1138, 2009.

Maynard, "An Introduction to the Watermelon," in: D.N. Maynard (ed.), *Watermelons: Characteristics, Production and Marketing*. ASHS Press, Alexandria, Virginia, pp. 9-20, 2001.

Monforte et al., "Identification of quantitative trait loci involved in fruit quality traits in melon (*Cucumis melo* L.)," *Theor. Appl. Genet.* 108:750-758, 2004.

Périn et al., "Genetic control of fruit shape acts prior to anthesis in melon (*Cucumis melo* L.)," *Mol. Genet. Genomics* 266:933-941, 2002.

Poole et al., "Interaction of sex, shape, and weight genes in watermelon," *J. Agric. Res.* 71:533-552, 1945.

Prothro et al., "Mapping of the Egusi Seed Trait Locus (eg) and Quantitative Trait Loci Associated with Seed Oil Percentage in Watermelon," *J. Amer. Soc. Hort. Sci.* 137(5):311-315, 2012.

Prothro et al., "Quantitative Trait Loci (QTL) Associated with Sex Expression in an Inter-subspecific Watermelon Population," *J. Am. Soc. Hort. Sci.* 138(2):125-130, 2013.

Ren et al., "A high resolution genetic map anchoring scaffolds of the sequenced watermelon genome," *PLoS ONE* 7(1): e294532012, 2012.

Robinson et al., *Cucurbits*. CAB International Publishing, Wallingford, UK, 1997.

Rosa, "The inheritance of flower types in *Cucumis* and *Citrullus*," *Hilgardia* 3:233-250, 1928.

Rudich et al., "Sex expression in watermelon as affected by photoperiod and temperature," *Scientia Horticulturae* 5(4):339-344, 1976.

Salman-Minkov et al., "ACC synthase genes are polymorphic in watermelon (*Citrullus* spp.) and differentially expressed in flowers and in response to auxin and gibberellin," *Plant Cell Physiol.* 49(5):740-750, 2008.

Sandlin et al., "Comparative mapping in watermelon [*Citrullus lanatus* (Thunb.) Matsum. et Nakai]," *Theor. App. Genet.* 125(8):1603-1618, 2012.

Smith, "Embryo culture of a tomato species hybrid," *Proc. Am. Soc. Hort. Sci.* 44:413-416, 1944.

Sugiyama, "Varietal Differences in Female Flower Bearing Ability and Evaluation Method in Watermelon," *Japan Agricultural research Quarterly* 32:267-273, 1998.

Trebitsh et al., "Identification of a 1-aminocyclopropane-1-carboxylic acid synthase gene linked to the female (F) locus that enhances female sex expression in cucumber," *Plant Physiol.* 113:987-995, 1997.

Willis et al., "Genetic architecture of novel traits in the hopi sunflower," *J. Hered.* 101(6):727-736, 2010.

Zeng, "Theoretical basis for separation of multiple linked gene effects in mapping quantitative trait loci," *Proc. Natl. Acad. Sci. USA* 90:10972-10976, 1993.

Sandlin, "Genetic Mapping in Citrullus lanatus", Thesis, University of Georgia, Dec. 2010, (available online at http://ugakr-maint.libs.uga.edu/bitstream/handle/123456789/7831/sandlin_katherine_c_201012_ms.pdf?sequence=1).

Hawkins et al., "Linkage Mapping in a Watermelon Population Segregating for Fusarium wilt Resistance", Journal of the American Society for Horticultural Science, 2001, pp. 344-350, vol. 126, No. 3.

Wehner et al., "Watermelons: Characteristics, Production and Marketing", American Society for Horticultural Science, 2001, Donald N. Maynard (Editor), Alexandria, VA.

Slater et al, "Plant Biotechnology: the genetic manipulation of plants 39", Oxford University Press, 2003, pp. 37-53, Chapter 2.

Maynard et al., "Triploid Watermelon Cultigen Evaluation", GCREC Research Report BRA-2003, Spring 2003, available at http://gcrecifas.ufl.edu/watermelons/Tri03/triploid%20manuscript%20SP03.htm.

Picha David H., "Storage temperature influences watermelon quality", Louisiana Agricultural Experiment Station, Winter 1987/1988, pp. 4-5, vol. 31 No. 2.

Leskovar et al., "Lycopene, carbohydrates, ascorbic acid and yield components of diploid and triploid watermelon cultivars are affected by deficit irrigation", Journal of Horticultural Science & Biotechnology, 2004, pp. 75-81, vol. 79 No. 1.

Smith, "Embryo culture of a tomato species hybrid", Proceedings of the American Society for Horticultural Science, 1944, pp. 413-416, vol. 44.

Cartaxo et al, "Controlled Atmosphere Storage Suppresses Microbial Growth on Fresh-Cut Watermelon", Proceedings of the Florida State Horticultural Society, 1997, pp. 252-257, vol. 110.

Extended European Search Report and Search Opinion dated Sep. 14, 2009 for European patent application No. 05764293.6-1212.

Fonseca et al., "Shock and Vibration Forces Influence the Quality of Fresh-Cut Watermelon", Proceedings of the Florida State Horticultural Society, 1999, pp. 147-152, vol. 112.

Gilreath et al., "Evaluation of Icebox Watermelon Cultivars in West Central and Southwest Florida", Proceedings of the Florida State Horticultural Society, 1986, pp. 331-334, vol. 99.

Jaskani et al., "Comparative Study on Vegetative, Reproductive and Qualitative Traits of Seven Diploid and Tetraploid Watermelon Lines", Euphytica, 2005, pp. 259-268, vol. 145

Jeffreys Seed Company Online, Hybrid Watermelon, website page http://www.jeffreys-seed.com/vegetable_seed/watermelon_02.html dated Mar. 30, 2004.

Karakurt et al., "Cell wall-degrading enzymes and pectin solubility and depolymerization in immature and ripe watermelon (*Citrullus lanatus*) fruit in response to exogenous ethylene", Physiologia Plantarum, 2002, pp. 398-405, vol. 116.

Karchi et al., "'Alena' Watermelon", HortScience, 1981, pp. 573, vol. 16 No. 4.

Karchi et al., "The Importance of Cultural Practices in Materializing Yield Potential in a Tetraploid Watermelon Cultivar", Cucurbit Genetics Cooperative Report, 1983, pp. 59-61 (article 30), vol. 6.

Leskovar et al., "Deficit Irrigation Influences Yield and Lycopene Content of Diploid and Triploid Watermelon", Vegetable Production & Marketing News, 2002.

Zhumei et al., "Selection and cultivation of the high quality early ride variety Nongfong No. 1B", Pingzhong Shuanyu, 2004, pp. 11-13, vol. 3.

Mao et al., "Incidence of water-soaking and phospholipid catabolism in ripe watermelon (*Citrullus lanatus*) fruit: induction by ethylene and prophylactic effects of 1-methylcyclopropene", Postharvest Biology and Technology, 2004, pp. 1-9, vol. 33.

Martyn et al., "Resistance to Races 0, 1, and 2 of Fusarium Wilt of Watermelon in *Citrullus* sp. PI-296341-FR", HortScience, 1991, pp. 429-432, vol. 26 No. 4.

Netzer et al., "PI 296341, a Source of Resistance in Watermelon to Race 2 of *Fusarium oxysporum* f. sp. nimeum", Plant Disease, 1989, pp. 518, vol. 73 No. 6.

Nip et al., "Physical, Chemical and Organoleptic Attributes of 'Charleston Gray' Watermelons at Different Stages of Maturity", American Society for Horticultural Science, 1968, pp. 547-551, vol. 93.

Perkins-Veazie et al., "Shelf Life of Minimally Processed Watermelon", HortScience, Jul. 1998, pp. 605, vol. 33 No. 4.

Perkins-Veazie et al., "Flesh quality and lycopene stability of fresh-cut watermelon", Postharvest Biology and Technology, 2004, pp. 159-166, vol. 31.

Risse et al., "Storage Characteristics of Small Watermelon Cultivars", Journal of the American Society for Horticulture Science, 1990, pp. 440-443, vol. 115 No. 3.

Risse et al., "Sensitivity of Watermelons to Ethylene during Storage", HortScience, 1982, pp. 946-948, vol. 17 No. 6.

Showalter, R.K., "Deformation and Breakage Properties of Watermelon Flesh", Florida State Horticultural Society, 1968, pp. 235-239, vol. 3148.

Strang et al., "Triploid Mini-Watermelon Variety Trial", 2004.

(56) References Cited

OTHER PUBLICATIONS

Yamasaki et al., "Mineral Concentrations and Cytokinin Activity in the Xylem Exudate of Grafted Watermelons as Affected by Rootstocks and Crop Load", Journal of the Japanese Society for Horticulture Science, 1994, pp. 817-826, vol. 52 No. 4.
Levi et al., "A Genetic Linkage Map for Watermelon Based on Randomly Amplified Polymorphic DNA Markers", Journal of the American Society for Horticultural Science, 2001, pp. 730-737, vol. 126 No. 6.
Third-Party Submission regarding European Application No. 13195763, dated Mar. 20, 2018.
U.S. National Germplasm System for Accession PI593359 (accessed on Mar. 8, 2018) available at https://npgsweb.ars-grin.gov/gringlobal/accessiondetail.aspx?id=1514498.
Villa et al., Defining and identifying crop landraces, *Plant Genetic Resources* 3(3):373-384, 2006.
Information Disclosure Statement (IDS) filed by Applicant in co-pending U.S. Appl. No. 13/600,612 to Seminis Vegetable Seeds, Inc. on Dec. 20, 2013, provided to evince that Applicant admits Sandlin (Document 2) was published in Dec. 2010.†
Sandlin, Katherine, Dec. 2010 Genetic Mapping in Citrullus Lanatus thesis submitted in fulfilment of the requirements for Masters of Science at University of Georgia, Athens, Georgia.†
Prothro, J. M., Dec. 2010. Genetic Mapping of Phenotypic and Quantitative Trait Loci Underlying Horticulturally Important Traits in Watermelon thesis submitted in fulfilment of the requirements for Masters of Science at University of Georgia, Athens, Georgia.†

\* cited by examiner
† cited by third party

```
                        SEQUENCE LISTING

<160> NUMBER OF SEQ ID NOS: 13

<210> SEQ ID NO 1
<211> LENGTH: 121
<212> TYPE: DNA
<213> ORGANISM: Citrullus lanatus
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t

<400> SEQUENCE: 1
tgttgttaaa angaaancag ataggggtag gggtagccga cagattgcaa cagtttgctg      60
yccagtgtta ttaaagccac acctaggcat ggtttccaaa aaaangtgtt gaaaagtgac     120
g                                                                    121

<210> SEQ ID NO 2
<211> LENGTH: 121
<212> TYPE: DNA
<213> ORGANISM: Citrullus lanatus

<400> SEQUENCE: 2
tatgtagtag atacattagt ccagggatgt aatgtaccta ggcgagactt tactaattcc      60
rgtgcggcca acagatgaca acggggaacc aggagatggt gaatcactat taggtgaagt     120
t                                                                    121

<210> SEQ ID NO 3
<211> LENGTH: 121
<212> TYPE: DNA
<213> ORGANISM: Citrullus lanatus

<400> SEQUENCE: 3
atgcacatcc aaccctgtct gaggtgcttg atgaactatt taaatcagcc aaggtcagtt      60
yaacattttt gtagatcatg cttgacctac aagactagtt cctatgtcaa tggaatccaa     120
c                                                                    121
```

```
<210> SEQ ID NO 4
<211> LENGTH: 120
<212> TYPE: DNA
<213> ORGANISM: Citrullus lanatus

<400> SEQUENCE: 4
ggattatttg ggtcctttaa cttcaagtgg gtggagtagg ctattatagc tttgagactc    60
ygattataat tgttagtgtt ttcaactatt ataacctaca actaactaca atattactgt   120

<210> SEQ ID NO 5
<211> LENGTH: 121
<212> TYPE: DNA
<213> ORGANISM: Citrullus lanatus

<400> SEQUENCE: 5
tcgagcaaat gaagagtatg gctggaaaac ataaagatga ttctggtgaa ggttcggagc    60
stacttcgca gatcaaactg acggtggacg agttcgaatc attgagcaga aggtcagag   120 a                                                                  121

<210> SEQ ID NO 6
<211> LENGTH: 121
<212> TYPE: DNA
<213> ORGANISM: Citrullus lanatus
<220> FEATURE:
<221> NAME/KEY: misc_feature
<222> LOCATION: (79)..(79)
<223> OTHER INFORMATION: n is a, c, g, or t

<400> SEQUENCE: 6
aataatattt taagggaca acgcatctga tggctagctt ttgcgtttct ccttattaat    60
waaggagtct tgataaaanc aatctttcaa tctttaactc ttcctgagaa ttaggatcgc   120
g                                                                  121

<210> SEQ ID NO 7
<211> LENGTH: 121
<212> TYPE: DNA
<213> ORGANISM: Citrullus lanatus

<400> SEQUENCE: 7
ctatagtgca gctgcacgtc cgcaaccggc tctatatttt ctacgagcag attctagctt    60
ygaacctcat cgaaaatgcg tccaatcttg atgaaaggcc atgaacggcc attaactttc   120
c                                                                  121

<210> SEQ ID NO 8
<211> LENGTH: 121
<212> TYPE: DNA
<213> ORGANISM: Citrullus lanatus

<400> SEQUENCE: 8
agattaccga ttaataacta ggcaacattg gcttgcccat tgcttgttat ggttccaggc    60
maacctggcc gcacaccata tttagttatt ttatcgattt cttctttga cattacttct   120 t                                                                  121

<210> SEQ ID NO 9
<211> LENGTH: 121
<212> TYPE: DNA
<213> ORGANISM: Citrullus lanatus

<400> SEQUENCE: 9
```
cagactgttg gcaaatattg tttggcacct ccatttcgag atagaaagct gtttagcaag    60
stgttatttt catcacacta cagaatattt ggttgaaaag gaactagaga atgtctcatg   120
a                                                                  121

<210> SEQ ID NO 10
<211> LENGTH: 121
<212> TYPE: DNA
<213> ORGANISM: Citrullus lanatus
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t

<400> SEQUENCE: 10
tcctgcgcat cctatcagga cctccactca tggagatggc ggagagggtt gggagagcgg    60
maagcacagg gcagttgagt ttcaggcatt tgaagaanga aagtgatggt gnnaatgaag   120
g                                                                  121

<210> SEQ ID NO 11
<211> LENGTH: 120
<212> TYPE: DNA
<213> ORGANISM: Citrullus lanatus
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 11
tgagataaga tgggatgatc acgggatgac tcagcttttg ttcaaagctt ccacctattt    60
kctattctat tttccttaat ttgtttaaaa aatnnctcnt ctatattttc gaaaattaca   120

<210> SEQ ID NO 12
<211> LENGTH: 121
<212> TYPE: DNA
<213> ORGANISM: Citrullus lanatus
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 12
aataaggtga aaggactaga ccagggttta agcnaaantc ctggagctac tcaagcatcc    60 maacccatc atggaaacct tggcaaaggt ggctgaagag taccccgagg gtagccggcg   120
t                                                                  121

<210> SEQ ID NO 13
<211> LENGTH: 121
<212> TYPE: DNA
<213> ORGANISM: Citrullus lanatus

<400> SEQUENCE: 13

```
ctgatcattc ccaaaacttc ggtttgtctc ttgagaaccc tgagcttctc ccggttggca        60
rggatgaatt tgtttgccaa acttctcaag ttcttgcact tcattttggg catgatagtc       120
t                                                                      121
```

METHODS AND COMPOSITIONS FOR WATERMELON SEX EXPRESSION

REFERENCE TO RELATED APPLICATIONS

This application claims the benefit of U.S. provisional Application No. 61/733,344, filed Dec. 4, 2012, and is herein incorporated by reference in its entirety.

FIELD OF THE INVENTION

The present invention relates to the field of plant breeding and, more specifically, to methods and compositions for producing watermelon plants with desired sex expression phenotypes.

INCORPORATION OF SEQUENCE LISTING

The sequence listing that is contained in the file named "SEMB010US_ST25.txt", which is 5 kilobytes as measured in Microsoft Windows operating system and was created on Dec. 2, 2013, is filed electronically herewith and incorporated herein by reference.

BACKGROUND OF THE INVENTION

Advances in molecular genetics have made it possible to select plants based on genetic markers linked to traits of interest, a process called marker-assisted selection (MAS). While breeding efforts to date have provided a number of useful watermelon lines and varieties with beneficial traits, there remains a need in the art for selection of varieties with further improved traits and methods for their production. In many cases, such efforts have been hampered by difficulties in identifying and using alleles conferring beneficial traits. These efforts can be confounded by the lack of definitive phenotypic assays, and other issues such as epistasis and polygenic or quantitative inheritance. In the absence of molecular tools such as MAS, it may not be practical to attempt to produce certain new genotypes of crop plants due to such challenges.

SUMMARY OF THE INVENTION

The invention provides, in one aspect, a watermelon plant comprising in its genome at least one introgressed allele locus associated with a desired sex expression phenotype, wherein the locus is in or genetically linked to loci NW0248967 (SEQ ID NO:1) and NW0248118 (SEQ ID NO:3) on linkage group 2 (LG2), or within 15 cM thereof; loci NW0252278 (SEQ ID NO:4) and NW0248560 (SEQ ID NO:5) on linkage group 7 (LG7), or within 15 cM thereof; loci NW0248392 (SEQ ID NO:6) and NW0248711 (SEQ ID NO:7) on linkage group 10 (LG10), or within 15 cM thereof; loci NW0249365 (SEQ ID NO:8) and NW0250112 (SEQ ID NO:9) on linkage group 11A (LG11A), or within 15 cM thereof; or loci NW0249365 (SEQ ID NO:8) and NW0250956 (SEQ ID NO:10) on linkage group 11A (LG11A), or within 15 cM thereof; loci NW0250956 (SEQ ID NO:10) and NW0250112 (SEQ ID NO:9) on linkage group 11A (LG11A), or within 15 cM thereof; or a progeny plant therefrom.

In certain embodiments, the plant is dioecious, or tetraploid, or diploid. In other embodiments, a desired sex expression phenotype is selected from the group consisting of percent male flowers, percent female flowers, percent hermaphroditic flowers, and percent female of total pistillate flowers. In other embodiments, the percent male or hermaphroditic flowers is at least about 90%, or the percent female flowers is at least about 90%.

In still further embodiments, the locus conferring a desired sex expression phenotype is in or genetically linked to a genomic region defined by: loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12 on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof. In other embodiments, parts of the watermelon plant are also provided. Plant parts may include pollen, an ovule, a leaf, an embryo, a root, a root tip, an anther, a flower, a fruit, a stem, a shoot, a seed, a protoplast, a cell, and a callus. The seed of such a plant are also provided.

In another aspect, the invention provides a method of detecting in at least one watermelon plant a genotype associated with a desired sex expression phenotype. In one embodiment, the method comprises the step of: (i) detecting in at least one watermelon plant an allele of at least one polymorphic nucleic acid that is associated with a desired sex expression phenotype, wherein the polymorphic nucleic acid is in or genetically linked to a genomic region defined by: loci NW0248967 (SEQ ID NO:1) and NW0248118 (SEQ ID NO:3) on linkage group 2 (LG2), or within 15 cM thereof; loci NW0252278 (SEQ ID NO:4) and NW0248560 (SEQ ID NO:5) on linkage group 7 (LG7), or within 15 cM thereof; loci NW0248392 (SEQ ID NO:6) and NW0248711 (SEQ ID NO:7) on linkage group 10 (LG10), or within 15 cM thereof; or loci NW0249365 (SEQ ID NO:8) and NW0250112 (SEQ ID NO:9) on linkage group 11A (LG11A), or within 15 cM thereof. In an embodiment, the method further comprises the step of: (ii) selecting at least one watermelon plant in which a genotype associated with a desired sex expression phenotype has been detected.

In another embodiment of the invention, the polymorphic nucleic acid located in or genetically linked to a genomic region flanked by: loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12 on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof.

In yet another aspect, the invention provides a method for producing a watermelon plant that comprises in its genome at least one locus associated with a desired sex expression phenotype, the method comprising: (i) crossing a first watermelon plant lacking a locus associated with a desired sex expression phenotype with a second watermelon plant comprising a locus associated with desired sex expression phenotype defined by loci NW0248967 (SEQ ID NO:1) and NW0248118 (SEQ ID NO:3) on linkage group 2 (LG2), or within 15 cM thereof; loci NW0252278 (SEQ ID NO:4) and NW0248560 (SEQ ID NO:5) on linkage group 7 (LG7), or within 15 cM thereof; loci NW0248392 (SEQ ID NO:6) and NW0248711 (SEQ ID NO:7) on linkage group 10 (LG10), or within 15 cM thereof; or loci NW0249365 (SEQ ID NO:8) and NW0250112 (SEQ ID NO:9) on linkage group 11A (LG11A), or within 15 cM thereof; (ii) detecting in progeny resulting from said crossing at least a first polymorphic locus in or genetically linked to said locus associated with a desired sex expression phenotype; and (iii) selecting a watermelon plant comprising said polymorphism and said locus associated with a desired sex expression phenotype. In an embodiment, the method may further comprise the step of (iv) crossing the watermelon plant with itself or another watermelon plant to produce a further generation. In another embodiment, steps (iii) and (iv) may be repeated from about 3 times to about 10 times. In other embodiments, the desired sex expression phenotype is selected from the group consisting of percent male flowers, percent female flowers, percent hermaphroditic flowers, and percent female of total pistillate flowers.

In other embodiments of the invention, the polymorphic nucleic acid associated with a desired sex expression phenotype is located in or genetically linked to a genomic region defined by: loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12) on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof.

In still yet another aspect, the invention provides a method of watermelon plant breeding, the method comprising the steps of: (i) selecting at least a first watermelon plant comprising at least one allele of a polymorphic nucleic acid that is in or genetically linked to a QTL associated with a desired sex expression phenotype, wherein the QTL maps to a position between loci NW0248967 (SEQ ID NO:1) and NW0248118 (SEQ ID NO:3) on LG2; loci NW0252278 (SEQ ID NO:4) and NW0248560 (SEQ ID NO:5) on LG7; loci NW0248392 (SEQ ID NO:6) and NW0248711 (SEQ ID NO:7) on LG10; or loci NW0249365 (SEQ ID NO:8) and NW0250112 (SEQ ID NO:9) on LG11A; and (ii) crossing the first watermelon plant with itself or a second watermelon plant to produce progeny watermelon plants comprising the QTL associated with a desired sex expression phenotype. In one embodiment, the desired sex expression phenotype comprises one or more traits selected from the group consisting of percent male flowers, percent female flowers, percent hermaphroditic flowers, and percent female of total pistillate flowers. In particular embodiments, the QTL maps to a position between: loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12) on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof.

In one embodiment of a method of the invention, at least one polymorphic nucleic acid that is genetically linked to a QTL associated with a desired sex expression phenotype maps within 40 cM, 20 cM, 15 cM, 10 cM, 5 cM, or 1 cM of the QTL associated with a desired sex expression phenotype.

In still yet another aspect, a method is provided for introgressing an allele into a watermelon plant, the method comprising: (i) genotyping at least one watermelon plant in a population with respect to at least one polymorphic nucleic acid located in or genetically linked to a genomic region defined by loci NW0248967 (SEQ ID NO:1) and NW0248118 (SEQ ID NO:3) on linkage group 2 (LG2), or within 15 cM thereof; loci NW0252278 (SEQ ID NO:4) and NW0248560 (SEQ ID NO:5) on linkage group 7 (LG7), or within 15 cM thereof; loci NW0248392 (SEQ ID NO:6) and NW0248711 (SEQ ID NO:7) on linkage group 10 (LG10), or within 15 cM thereof; or loci NW0249365 (SEQ ID NO:8) and NW0250112 (SEQ ID NO:9) on linkage group 11A (LG11A), or within 15 cM thereof; and (ii) selecting from the population at least one watermelon plant comprising at least one allele associated with a desired sex expression phenotype. In certain embodiments, the desired sex expression phenotype comprises one or more traits selected from the group consisting of percent male flowers, percent female flowers, percent hermaphroditic flowers, and percent female of total pistillate flowers. In another embodiment, the polymorphic nucleic acid is located in a genomic region flanked by: loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12) on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof. In another embodiment, a watermelon plant is obtained by the method.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects and features will be in part apparent and in part pointed out hereinafter.

BRIEF DESCRIPTION OF THE SEQUENCE LISTING

Figure 1:
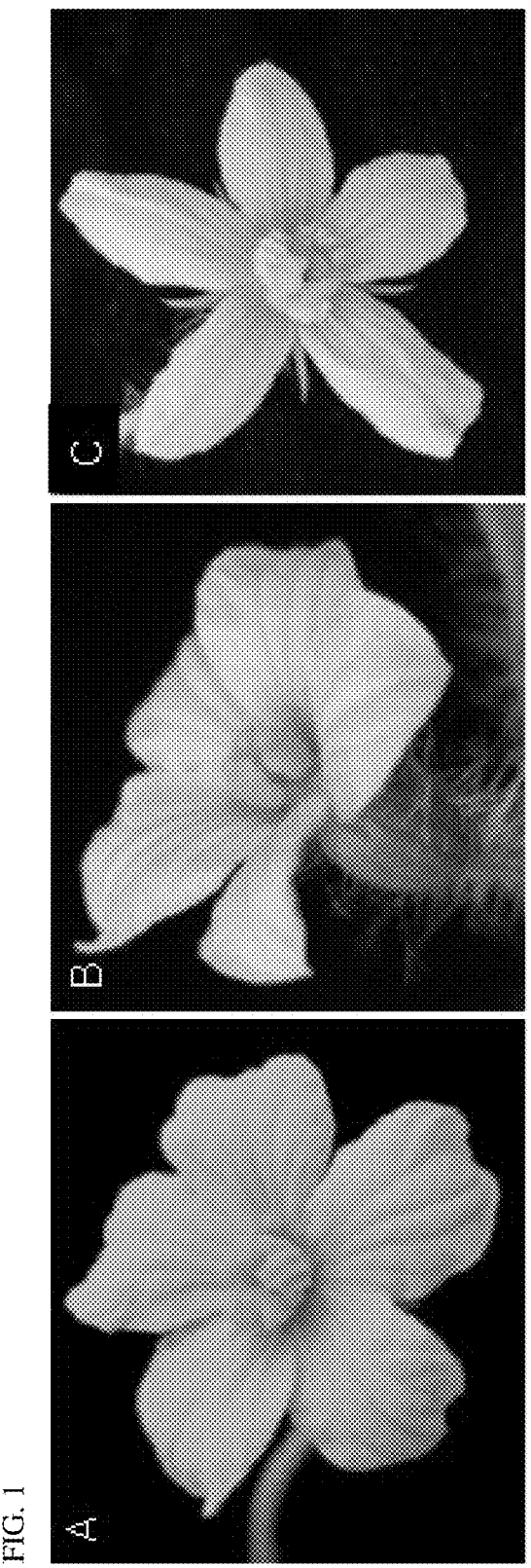
FIG. 1: Shows (A) male and (B) female flower of *C. lanatus* var. *lanatus* (ZWRM; PI 593359) and (C) an andromonoecious flower from *C. lanatus* var. *citroides* (CTR; PI 244019).

SEQ ID NO:1—Marker NW0248967.
SEQ ID NO:2—Marker NW0248583.
SEQ ID NO:3—Marker NW0248118.
SEQ ID NO:4—Marker NW0252278.
SEQ ID NO:5—Marker NW0248560.
SEQ ID NO:6—Marker NW0248392.
SEQ ID NO:7—Marker NW0248711.
SEQ ID NO:8—Marker NW0249365.
SEQ ID NO:9—Marker NW0250112.
SEQ ID NO:10—Marker NW0250956.
SEQ ID NO:11—Marker NW0251455.
SEQ ID NO:12—Marker NW0249392.
SEQ ID NO:13—Marker NW0248268.

DETAILED DESCRIPTION OF THE INVENTION

The invention represents an advance in the art in that it permits development of watermelon varieties with desired sex expression phenotypes. Sex expression is important for watermelon breeders, since the majority of commercially grown cultivars are $F_1$ hybrids. Andromonoecious forms are highly undesirable as seed parents since hermaphroditic flowers require emasculation before cross-pollination. In addition to the andromonoecious trait, the ratio of staminate:pistillate flowers is also of interest to breeders. Commercial watermelon cultivars usually have an approximate ratio of 7:1 staminate:pistillate flowers (Wehner, Watermelon, p. 381-4, In: Prohens, J. and Nuez, F. (eds.), Vegetables I: Asteraceae, Brassicaceae, Chenopodiaceae, and Cucurbitaceae. Springer, New York, N.Y., 2008), but this ratio can vary greatly. For the production of $F_1$ hybrids, dioecy (separate male and female plants) is desirable, but this has not been observed in watermelon (Rudich and Zamski, *Citrullus lanatus*, p. 272-274. In: Halevy, A. (ed.), Handbook of flowering. CRC Press, Boca Raton, Fla., 1985; Salman-Minkov et al., *Plant Cell Physiol* 49:740-750, 2008).

The present invention thus represents a significant advantage by providing watermelon plants and methods for their production comprising at least a first introgressed locus contributing to a desired sex expression phenotype. In accordance with the invention the introgressed locus allele may be newly introgressed into a given desired genomic background of a specific variety or cultivar. For example, as discussed further below, a watermelon having a desired sex expression phenotype can be produced to have one or more traits selected from a desired percent male flowers, percent female flowers, percent hermaphroditic flowers, percent female of total pistillate flowers, and any and all combinations thereof. Certain embodiments further provide methods of detecting in a watermelon plant a genotype associated with the desired sex expression phenotype. Certain embodiments also provide methods of identifying and selecting a watermelon plant comprising in its genome a genotype associated with a desired sex expression phenotype. Further, certain embodiments provide methods of producing a watermelon plant that comprises in its genome at least one introgressed locus associated with a desired sex expression phenotype and methods for introgressing such an allele into a watermelon plant. Watermelon plants and parts thereof made by any of said methods are also provided for, as well as polymorphic nucleic acid sequences that may be used in the production and identification of such plants.

By providing markers to infer a sex expression phenotype of interest, the invention results in significant economization by permitting substitution of costly, time-intensive, and potentially unreliable phenotyping assays with genotyping. Further, breeding programs can be designed to explicitly drive the frequency of specific favorable phenotypes by targeting particular genotypes. Fidelity of these associations may be monitored continuously to ensure maintained predictive ability and, thus, informed breeding decisions.

In accordance with the invention, one of skill in the art may thus identify a candidate germplasm source possessing a desirable sex expression phenotype as described herein, but which is lacking one or more traits which the plant breeder seeks to have in a variety or parent line thereof. The techniques of the invention may be used to identify desirable sex expression phenotypes by identifying genetic markers associated with the phenotype, or such techniques may employ phenotypic assays to identify desired plants either alone or in combination with genetic assays, thereby also identifying a marker genotype associated with the trait that may be used for production of new varieties with the methods described herein.

Generally, watermelon sex expression can be divided into qualitative categories as being monoecious (separate male and female flowers on the same plant), andromonoecious (separate male and hermaphrodite flowers on the same plant), and trimonoecious (separate male, female and hermaphrodite flowers on the same plant) (Ferreira et al., *Crop Breeding Appl Biotechnol* 2:39-48, 2002; Maynard, An introduction to the watermelon, p. 9-20. In: Maynard, D. N. (ed.), Watermelon characteristics, production and marketing. ASHS Press, Alexandria, Va., 2001; Robinson et al., Cucurbits. CAB International Publishing, Wallingford, UK, 1997; Rosa, *Hilgardia* 3:233-250, 1928).

In accordance with the invention, a desired sex expression phenotype refers to desired percent male flowers, percent female flowers, percent hermaphroditic flowers, percent female of total pistillate flowers, and/or any and all combinations thereof that one or more breeder, grower, or consumer may find advantageous for certain applications. As explained, in certain aspects, a dioecious sex expression phenotype may be desirable for applications including, but not necessarily limited to the production of $F_1$ hybrids. In addition, for breeding purposes, it may be desirable to produce watermelon plants with particular ratios of staminate:pistillate flowers. The particular phenotype may depend upon the desired end uses. However, as the traits in question have been shown to be controlled by the QTL regions identified herein, these traits may be introgressed into desired genetic backgrounds using the methods of the invention.

The present invention relates to watermelon QTL associated with sex expression. This trait is important during the production of hybrid watermelon plants, which are produced by crossing a seed parent plant with a pollen parent plant. Typically, a female inbred parent line and a pollen donor (male) inbred line are crossed to produce a given commercial hybrid. For example, hybrid seedless watermelon can be produced by crossing a diploid parent plant with a tetraploid parent plant. Sex expression is important for this process, particularly because emasculation of hermaphroditic flowers on a plant to be used as the female parent must be done to prevent self-fertilization. Thus, it is advantageous for the female parent plant to have very few anthers. For male parent plants, on the other hand, a large number of anthers and a corresponding low number of female flowers is beneficial to ensure an adequate supply of pollen and prevent self-fertilization.

QTL of the present invention may be useful in development of watermelon pollenizer lines. In particular, for typical watermelon breeding practices, pollenizer plants with male flowers are required to produce pollen for an outcross to produce hybrid watermelon plants. QTL as described herein may thus enable development of watermelon lines with increased percent male flowers and pollen production, thereby resulting in less field space needed to dedicate to pollenizer plants in triploid (seedless) watermelon production. Further, such QTL may allow production of watermelon plants with decreased frequency of anthers on female flowers of seed parent inbred plants during hybrid seed production, thereby resulting in an increase in percent hybridity of the produced seed (less selfed seed). The present invention therefore relates to markers and QTL linked to percent male, percent female, and/or percent hermaphroditic flowers and methods of use thereof in order to select parent lines that would better serve as male or female seed parents for hybrid production.

The invention thus provides for the introgression of at least a first locus conferring a desired sex expression phenotype into a given genetic background. Successful watermelon production depends on attention to various horticultural practices. These include soil management with special attention to proper fertilization, crop establishment with appropriate spacing, weed control, the introduction of bees or other insects for pollination, irrigation, pest management, and, if producing fruit from triploid plants, a suitable pollen source for producing seedless (triploid) watermelon. Watermelon flower size and shape; rind color, thickness and toughness; sex expression, color, and number; flesh color, texture, and sugar content; and freedom from fruit defects are all important characteristics to be considered in selection of watermelon varieties.

Watermelon crops can be established from seed or from transplants. Transplanting can result in an earlier crop compared with a crop produced from direct seeding. When a grower wants to raise a seedless fruited crop, transplanting can be preferred. Transplanting helps achieve complete plant stands rapidly, especially where higher seed costs, as with triploid seeds, make direct-seeding risky.

Watermelon breeders are challenged with anticipating changes in growing conditions, new pathogen pressure, and changing consumer preferences. With these projections, a breeder will attempt to create new cultivars that will fit the developing needs of growers, shippers, retailers, and consumers. Thus, the breeder is challenged to combine in a single genotype as many favorable attributes as possible for good growing distribution and eating.

Development of Watermelon Varieties with Desired Sex Expression Phenotypes

As indicated, sex expression is important in terms of production of $F_1$ hybrid plants, and has significance to growers, processors, retailers, and customers. The current inventors have identified quantitative trait loci (QTL) with major effects for sex expression, as well as single nucleotide polymorphism (SNP) markers genetically linked to and predictive of such loci that can be used for the tracking and introgression of the QTL into desirable germplasm, such as by marker-assisted selection and/or marker-assisted backcrossing.

As reported herein in one example, an inter-subspecific $F_2$ population was developed by a cross between *C. lanatus* var. *lanatus* ZWRM 50 from China (ZWRM; PI 593359) and a wild *C. lanatus* var. *citroides* accession from South Africa (CTR; PI 244019). A single $F_1$ plant was self-pollinated to obtain $F_2$ seed. Identification of Quantitative Trait Loci (QTL) associated with percent male (% M), percent female (% F), percent hermaphrodite (% HM) and percent female of pistillate (female+hermaphrodite) (% F/P) flowers was conducted on these $F_2$ plants. Four chromosomal regions were identified that were associated with sex expression in watermelon. Major QTL for % F, % HM and % F/P were co-localized on LG 11A and explained 31.3-37.7% of the phenotypic variation observed for the three traits. Markers linked to two of the four chromosomal regions identified were located within 1 Mb of a 1-aminocyclopropane-1-carboxylic acid synthase (ACS) gene in the watermelon genome.

The invention thus contemplates the tracking and introduction of any such QTL and any combinations thereof into a given genetic background. One of ordinary skill will understand that any desired sex expression phenotype including one or more traits of percent male flowers, percent female flowers, percent hermaphroditic flowers, percent female of total pistillate flowers, and/or any and all combinations thereof can be introgressed from one genotype to another using a primary locus described herein via marker assisted selection. Accordingly, a germplasm source can be selected that has a desired sex expression phenotype in terms of percent male flowers, percent female flowers, percent hermaphroditic flowers, percent female of total pistillate flowers. A breeder can now select a desired sex expression phenotype or track such desired sex expression phenotype during breeding using marker assisted selection for the region described herein. Provided with the present disclosure, one of ordinary skill can introduce a desired sex expression phenotype into any genetic background.

Thus, QTL identified herein can be used for marker assisted selection for sex expression in watermelon. This discovery of sex expression QTL will facilitate the development of watermelon having desired sex expression phenotypes.

For most breeding objectives, commercial breeders may work within germplasm that is often referred to as the "cultivated type" or "elite." This germplasm is easier to breed with because it generally performs well when evaluated for horticultural performance. The performance advantage a cultivated type provides is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, Proc. Am. Soc. Hort. Sci. 44:413-16). In this cross, a nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent.

In watermelon, the plant introduction accessions are typically lines that produce fruits with undesirable production and eating qualities. Even though these lines have poor horticultural qualities, some watermelon breeders, like some other crop breeders, attempt to breed with these PI lines because they potentially contain novel alleles. To date, the most commonly attempted breeding objective for use of the PI lines is to introgress new disease resistance genes. The process of introgressing novel resistance genes from the PI lines into acceptable commercial types is a long and often arduous process. This process can be difficult because the trait may be polygenic, or have low heritability, or have linkage drag or some combination thereof.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as QTLs. Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

Genomic Region, QTL, Polymorphic Nucleic Acids, and Alleles Associated with Watermelon Sex Expression Phenotype Applicants have discovered a genomic region, QTL, alleles, polymorphic nucleic acids, linked markers, and the like that when present in certain allelic forms are associated with watermelon sex expression phenotype.

Using an inter-subspecific *C. lanatus* var. *lanatus*×*C. lanatus* var. *citroides* $F_2$ population, nine M-QTL were identified on four linkage groups (LGs) (LG2, LG7, LG10, LG11A) for the three traits of percent male flowers, percent female flowers, percent hermaphroditic flowers, percent female of total pistillate flowers.

LG2

A genomic region associated with a desired sex expression phenotype was located at watermelon linkage group 2, flanked by loci NW0248967 (SEQ ID NO:1) and NW0248118 (SEQ ID NO:3).

Certain of the various embodiments of the present disclosure thus utilize one or more QTL or polymorphic nucleic acid markers or alleles located in one or more of these regions or subregions on LG2.

Two major watermelon sex expression QTL were found to be located within this region. Certain of the various embodiments of the present disclosure utilize one or more QTL or polymorphic nucleic acid markers or alleles located in this genomic region. Flanking markers on LG2 that identify a genomic region associated with a desired sex expression phenotype include loci NW0248967 (SEQ ID NO:1) and NW0248118 (SEQ ID NO:3). Intervening markers on LG2 that identify a genomic region associated with a desired sex expression phenotype include NW0248118 (SEQ ID NO:3) and NW0251455 (SEQ ID NO:11). These genomic regions, or subregions thereof, associated with a desired sex expression phenotype can be described as being flanked by: loci NW0248967 (SEQ ID NO:1) and NW0248118 (SEQ ID NO:3); loci NW0248967 (SEQ ID NO:1) and NW0251455 (SEQ ID NO:11); or loci NW0248118 (SEQ ID NO:3) and NW0251455 (SEQ ID NO:11).

LG7

Another genomic region associated with a desired sex expression phenotype was located at watermelon linkage group 7, flanked by loci NW0252278 (SEQ ID NO:4) and NW0248560 (SEQ ID NO:5) on linkage group 7 (LG7). A major watermelon sex expression QTL was found to be located within this region. Certain of the various embodiments of the present disclosure thus utilize one or more QTL or polymorphic nucleic acid markers or alleles located in this genomic region. Flanking markers that identify a genomic region associated with a desired sex expression phenotype include loci NW0252278 (SEQ ID NO:4) and NW0248560 (SEQ ID NO:5) on linkage group 7 (LG7). Intervening markers on LG7 that identify a genomic region associated with a desired sex expression phenotype include NW0249392 (SEQ ID NO:12). This genomic region, or subregions thereof, associated with a desired sex expression phenotype can be described as being flanked by: loci NW0252278 (SEQ ID NO:4) and NW0248560 (SEQ ID NO:5); loci NW0252278 (SEQ ID NO:4) and NW0249392 (SEQ ID NO:12); or loci NW0248560 (SEQ ID NO:5) and NW0249392 (SEQ ID NO:12).

LG10

A genomic region associated with a desired sex expression phenotype was located at watermelon linkage group 10, flanked by loci NW0248392 (SEQ ID NO:6) and NW0248711 (SEQ ID NO:7)

Two major watermelon sex expression QTL were found to be located within this region. Certain of the various embodiments of the present disclosure utilize one or more QTL or polymorphic nucleic acid markers or alleles located in this genomic region. Flanking markers that identify a genomic region associated with a desired sex expression phenotype include loci NW0248392 (SEQ ID NO:6) and NW0248711 (SEQ ID NO:7). Intervening markers on LG10 that identify a genomic region associated with a desired sex expression phenotype include NW0248268 (SEQ ID NO:13). This genomic region, or subregions thereof, associated with a desired sex expression phenotype can be described as being flanked by: loci NW0248392 (SEQ ID NO:6) and NW0248711 (SEQ ID NO:7); loci NW0248392 (SEQ ID NO:6) and NW0248268 (SEQ ID NO:13); or loci NW0248711 (SEQ ID NO:7) and NW0248268 (SEQ ID NO:13).

LG11A

A genomic region associated with a desired sex expression phenotype was located at watermelon linkage group 11A, flanked by loci NW0249365 (SEQ ID NO:8) and NW0250112 (SEQ ID NO:9).

Four major watermelon sex expression QTL were found to be located within this region. Certain of the various embodiments of the present disclosure utilize one or more QTL or polymorphic nucleic acid marker or allele located in this genomic region. Flanking markers on LG11A that identify a genomic region associated with a desired sex expression phenotype include loci NW0249365 (SEQ ID NO:8) and NW0250112 (SEQ ID NO:9); loci NW0249365 (SEQ ID NO:8) and NW0250956 (SEQ ID NO:10); or loci NW0250956 (SEQ ID NO:10) and NW0250112 (SEQ ID NO:9). Intervening markers on LG11A that identify a genomic region associated with a desired sex expression phenotype include loci NW0250956 (SEQ ID NO:10). This genomic region, or subregions thereof, associated with a desired sex expression phenotype can be described as being flanked by: loci NW0249365 (SEQ ID NO:8) and NW0250112 (SEQ ID NO:9); loci NW0249365 (SEQ ID NO:8) and NW0250956 (SEQ ID NO:10); or loci NW0250112 (SEQ ID NO:9) and NW0250956 (SEQ ID NO:10).

The above markers and allelic states are exemplary. One of skill in the art would recognize how to identify watermelon plants with other polymorphic nucleic acid markers and allelic states thereof related to watermelon sex expression consistent with the present disclosure. One of skill the art would also know how to identify the allelic state of other polymorphic nucleic acid markers located in the genomic region(s) or linked to the QTL or other markers identified herein, to determine their association with watermelon sex expression.

Watermelons are natural diploids, having their chromosomes arranged in pairs. Watermelon plants, however, can undergo a duplication of their entire set of chromosomes and exist as tetraploids. While it is uncommon for watermelons to produce spontaneous tetraploids, this process can be routinely produced in the laboratory using cell biology techniques. Triploid seeds can be produced by crossing a tetraploid parent by a diploid parent. When triploid plants are grown, seed formation in the fruit aborts because of the ploidy level differences, resulting in seedless fruits.

In certain embodiments of methods of the invention, a diploid parent plant is homozygous for the QTL or a polymorphic nucleic acid marker allele associated with the desired sex expression phenotype. The diploid parent is crossed with a tetraploid lacking the QTL or a polymorphic nucleic acid marker allele associated with the desired sex expression phenotype, to produce triploid hybrid progeny. This results in one copy of the QTL or polymorphic marker allele associated with the desired sex expression phenotype (from the diploid parent) and two non-QTL/marker alleles (from the tetraploid parent) in the triploid hybrid. Alternatively, in certain embodiments of methods of the invention, a tetraploid parent plant is homozygous for the QTL or a polymorphic nucleic acid marker allele associated with the desired sex expression phenotype. The tetraploid parent is crossed with a diploid lacking the QTL or a polymorphic nucleic acid marker allele associated with the desired sex expression phenotype, to produce triploid hybrid progeny. This results in two copies of the QTL or polymorphic marker allele associated with the desired sex expression phenotype (from the tetraploid parent) and one non-QTL/marker allele (from the diploid parent) in the triploid hybrid.

Certain embodiments of the invention contemplate the use of dihaploidization to produce an inbred line. A haploid plant has only one copy of each chromosome instead of the normal pair of chromosomes in a diploid plant. Haploid plants can be produced, for example, by treating with a haploid inducer. Haploid plants can be subjected to treatment that causes the single copy chromosome set to double, producing a duplicate copy of the original set. The resulting plant is termed a "double-haploid" and contains pairs of chromosomes that are generally in a homozygous allelic state at any given locus. Dihaploidization can reduce the time required to develop new inbred lines in comparison to developing lines through successive rounds of backcrossing.

One of skill in the art would understand that polymorphic nucleic acids that are located in the genomic regions identified may be used in certain embodiments of the methods of the invention. Given the provisions herein of a genomic region, QTL, and polymorphic markers identified herein, additional markers located either within or near a genomic region described herein that are associated with the phenotype can be obtained by typing new markers in various germplasm. The genomic region, QTL, and polymorphic markers identified herein can also be mapped relative to any publicly available physical or genetic map to place the region described herein on such map. One of skill in the art would also understand that additional polymorphic nucleic acids that are genetically linked to the QTL associated with a desired sex expression phenotype and that map within 40 cM, 20 cM, 10 cM, 5 cM, or 1 cM of the QTL or the markers associated with a desired sex expression phenotype may also be used.

Introgression of a Genomic Locus Associated with a Desired Sex Expression Phenotype Provided herein are unique watermelon germplasm or watermelon plants comprising an introgressed genomic region that is associated with a desired sex expression phenotype and method of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., desired sex expression phenotype germplasm) and both linked and unlinked markers characteristic of the desired genetic background of a second germplasm.

Flanking markers that identify a genomic region associated with a desired sex expression phenotype can include any loci described above on LG2, LG7, LG10, or LG11A; and those that identify sub-regions thereof can include any loci or loci intervals described above on LG2, LG7, LG10, or LG11A.

For example, flanking markers that identify a genomic region or subregion include those defined by loci NW0248967 (SEQ ID NO:1) and NW0248118 (SEQ ID NO:3) on linkage group 2 (LG2), or within 15 cM thereof; loci NW0252278 (SEQ ID NO:4) and NW0248560 (SEQ ID NO:5) on linkage group 7 (LG7), or within 15 cM thereof; loci NW0248392 (SEQ ID NO:6) and NW0248711 (SEQ ID NO:7) on linkage group 10 (LG10), or within 15 cM thereof; or loci NW0249365 (SEQ ID NO:8) and NW0250112 (SEQ ID NO:9) on linkage group 11A (LG11A), or within 15 cM thereof.

In further embodiments, markers are provided in a genomic region flanked by loci NW0248967 (SEQ ID NO:1) and NW0251455 (SEQ ID NO:11) on LG2; loci NW0248118 (SEQ ID NO:3) and NW0251455 (SEQ ID NO:11) on LG2; loci NW0252278 (SEQ ID NO:4) and NW0249392 (SEQ ID NO:12 on LG7; loci NW0248560 (SEQ ID NO:5) and NW0249392 (SEQ ID NO:12 on LG7; loci NW0248392 (SEQ ID NO:6) and NW0248268 (SEQ ID NO:13) on LG10; or loci NW0248711 (SEQ ID NO:7) and NW0248268 (SEQ ID NO:13) on LG10; or within 15 cM thereof.

Flanking markers that fall on both the telomere proximal end and the centromere proximal end of any of these genomic intervals may be useful in a variety of breeding efforts that include, but are not limited to, introgression of genomic regions associated with a desired sex expression phenotype into a genetic background comprising markers associated with germplasm that ordinarily contains a genotype associated with another phenotype.

Markers that are linked and either immediately adjacent or adjacent to the identified desired sex expression phenotype QTL that permit introgression of the QTL in the absence of extraneous linked DNA from the source germplasm containing the QTL are provided herewith. Those of skill in the art will appreciate that when seeking to introgress a smaller genomic region comprising a QTL associated with a desired sex expression phenotype described herein, that any of the telomere proximal or centromere proximal markers that are immediately adjacent to a larger genomic region comprising the QTL can be used to introgress that smaller genomic region.

A marker within about 40 cM of a marker of a sex expression phenotype QTL described herein may be useful in a variety of breeding efforts that include, but are not limited to, introgression of genomic regions associated with a desired sex expression phenotype into a genetic background comprising markers associated with germplasm that ordinarily contains a genotype associated with another phenotype. For example, a marker within 40 cM, 20 cM, 15 cM, 10 cM, 5 cM, 2 cM, or 1 cM of a sex expression phenotype QTL or marker described herein can be used for marker-assisted introgression of a desired sex expression phenotype.

A marker within about 40 cM of a sex expression phenotype QTL marker on LG2 described herein can be used for marker-assisted introgression of a desired sex expression phenotype. For example, a marker within 40 cM, 20 cM, 15 cM, 10 cM, 5cM, 2 cM, or 1 cM of a sex expression phenotype QTL marker on LG2 described herein can be used for marker-assisted introgression of a desired sex expression phenotype. As described above, a sex expression phenotype QTL marker on LG2 can include one or more of NW0248967 (SEQ ID NO:1); NW0248118 (SEQ ID NO:3); or NW0251455 (SEQ ID NO:11).

A marker within about 40 cM of a sex expression phenotype QTL marker on LG7 described herein can be used for marker-assisted introgression of a desired sex expression phenotype. For example, a marker within 40 cM, 20 cM, 15 cM, 10 cM, 5cM, 2 cM, or 1 cM of a sex expression phenotype QTL marker on LG7 described herein can be used for marker-assisted introgression of a desired sex expression phenotype. As described above, a sex expression phenotype QTL marker on LG7 can include one or more of loci NW0252278 (SEQ ID NO:4); NW0248560 (SEQ ID NO:5); or NW0249392 (SEQ ID NO:12).

A marker within about 40 cM of a sex expression phenotype QTL marker on LG10 described herein can be used for marker-assisted introgression of a desired sex expression phenotype. For example, a marker within 40 cM, 20 cM, 15 cM, 10 cM, 5cM, 2 cM, or 1 cM of a sex expression phenotype QTL marker on LG10 described herein can be used for marker-assisted introgression of a desired sex expression phenotype. As described above, a sex expression phenotype QTL marker on LG10 can include one or more of NW0248392 (SEQ ID NO:6); NW0248711 (SEQ ID NO:7); or NW0248268 (SEQ ID NO:13).

A marker within about 40 cM of a sex expression phenotype QTL marker on LG11A described herein can be used for marker-assisted introgression of a desired sex expression phenotype. For example, a marker within 40 cM, 20 cM, 15 cM, 10 cM, 5cM, 2 cM, or 1 cM of a sex expression phenotype QTL marker on LG11A described herein can be used for marker-assisted introgression of a desired sex expression phenotype. As described above, a sex expression phenotype QTL marker on LG11A can include one or more of NW0249365 (SEQ ID NO:8); NW0250112 (SEQ ID NO:9); or NW0250956 (SEQ ID NO:10).

Watermelon plants or germplasm comprising an introgressed region that is associated with a desired sex expression phenotype wherein at least 10%, 25%, 50%, 75%, 90%, or 99% of the remaining genomic sequences carry markers characteristic of plant or germplasm that otherwise or ordinarily comprise a genomic region associated with another phenotype, are thus provided. Furthermore, watermelon plants comprising an introgressed region where closely linked regions adjacent and/or immediately adjacent to the genomic regions, QTL, and markers provided herewith that comprise genomic sequences carrying markers characteristic of watermelon plants or germplasm that otherwise or ordinarily comprise a genomic region associated with the phenotype are also provided.

Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), simple sequence length polymorphisms (SSLPs), Single Nucleotide Polymorphisms (SNP), Insertion/Deletion Polymorphisms (Indels), Variable Number Tandem Repeats (VNTR), and Random Amplified Polymorphic DNA (RAPD), isozymes, and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) Genomics, 8(2), 271-278), denaturing gradient gel electrophoresis (Myers (1985) EPO 0273085), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer, et al. (1992) Biotechniques 12(1), 82-87), or PCR amplification of multiple specific alleles (PAMSA, Dutton and Sommer (1991) Biotechniques, 11(6), 700-7002).

Recently, single nucleotide polymorphism (SNP) genetic maps were produced using diverse *C. lanatus* parents, including a population produced from an elitexelite (*C. lanatus* var. *lanatus*) cross and a population from an inter-subspecific cross between an elite cultivar and *C. lanatus* var. *citroides* (Sandlin et al., *Theor Appl Genet* 125(8):1603-18, 2012). As described herein, genetically diverse mapping populations that segregate for sex expression were used to identify main effect QTL (M-QTL) and epistatic QTL (E-QTL) associated with sex expression in watermelon. Results described herein identify QTL on LG2, LG7, LG10, and LG11A that may control sex expression in watermelon.

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a watermelon plant a genotype associated with a desired sex expression phenotype, identify a watermelon plant with a genotype associated with desired sex expression phenotype, and to select a watermelon plant with a genotype associated with a desired sex expression phenotype. In certain embodiments of methods of the invention, polymorphic nucleic acids can be used to produce a watermelon plant that comprises in its genome an introgressed locus associated with a desired sex expression phenotype. In certain embodiments of the invention, polymorphic nucleic acids can be used to breed progeny watermelon plants comprising a locus associated with a desired sex expression phenotype.

Certain genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a desired sex expression phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. No. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996, 476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, a watermelon having a "desired sex expression phenotype" has one or more traits of a desired percent male flowers, percent female flowers, percent hermaphroditic flowers, and percent female of total pistillate flowers.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "maturity" means maturity of fruit development. Maturity indicates the time a watermelon fruit is ready to be harvested. In watermelon, the maturity comes associated with changes in flesh color and sugar content.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

EXAMPLES

The following disclosed embodiments are merely representative of the invention which may be embodied in various forms. Thus, specific structural, functional, and procedural details disclosed in the following examples are not to be interpreted as limiting.

Example 1

Plant Materials and Genetic Map

The development of the *C. lanatus* var. *lanatus*×*C. lanatus* var. *citroides* $F_2$ population has been described previously (Sandlin et al., *Theor Appl Genet* 125(8):1603-18, 2012). Briefly, a cross was made between *C. lanatus* var. *lanatus* ZWRM 50 from China (ZWRM; PI 593359) and a wild *C. lanatus* var. *citroides* accession from South Africa (CTR; PI 244019). A single $F_1$ plant was self-pollinated to obtain $F_2$ seed. One hundred and eighty two $F_2$ individuals were genotyped and a genetic map consisting of 338 Single Nucleotide Polymorphism (SNP) markers was constructed (Sandlin et al., *Theor Appl Genet* 125(8):1603-18, 2012).

Example 2

Trait Phenotyping

ZWRM×CTR $F_2$ plants and parental genotypes were grown in the greenhouse at the University of Georgia's campus in Athens from May to August 2007. Seeds were germinated in seedling trays and transplanted four weeks later into 14.136-L nursery pots (C1600-Classic, Nursery Supplies Inc., Kissimmee, Fla.) filled with Fafard 3B mix (Conrad Fafard, Inc., Agawam, Mass.) and 12 g Osmocote Pro (19N-2.2P-6.6K; Scotts Miracle-Gro, Marysville, Ohio) per pot. Flower sex expression was recorded as the number of female, male, and hermaphrodite flowers in the first 20 flowering nodes of the main vine on each plant. The sex expression data was converted to percent male (% M), percent female (% F), percent hermaphrodite (% HM) and percent female of pistillate (female+hermaphrodite) (% F/P) flowers. Pearson correlations were calculated using JMP 9.0.2 (JMP Version 9.0.2., 2010).

Figure 2:
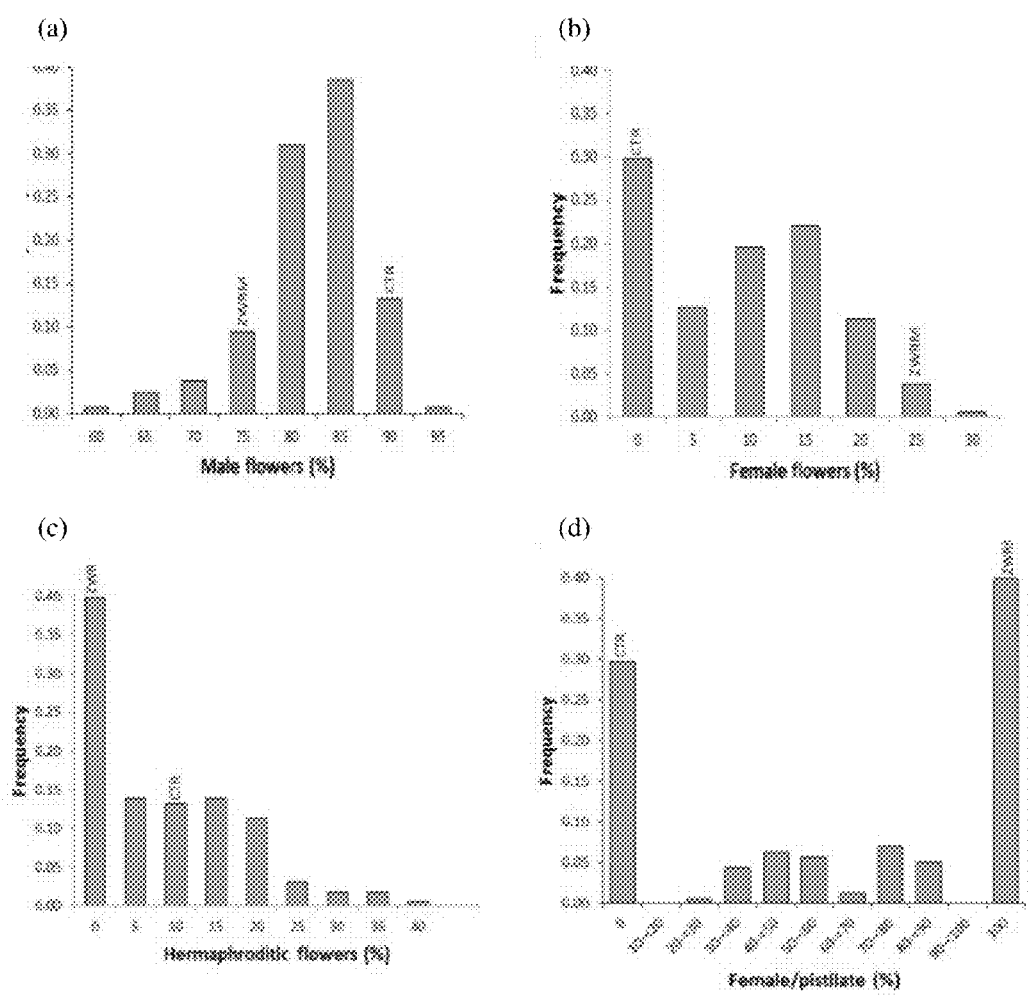
FIG. 2: Shows frequency distribution of (a) percent male flowers, (b) percent female flowers, (c) percent hermaphroditic flowers and (d) percent female of pistillate flowers in the first twenty flowers of the main vine of the *C. lanatus* var. *lanatus* (ZWRM; PI 593359)×*C. lanatus* var. *citroides* (CTR; PI 244019) $F_2$ population. The parental (ZWRM and CTR) phenotypes are indicated.

Results:

ZWRM was monoecious with 75% male and 25% female flowers, while CTR was andromonoecious with 90% male and 10% hermaphrodite flowers (FIG. 1, and FIG. 2). The % M flowers in the $F_2$ population varied from 60% to 95% (FIG. 3a) and included monoecious (~40%), andromonoecious (~30%) and trimonoecious (~30%; male, female and hermaphrodite) plants (FIGS. 2b, 2c, and 2d). The % F/P trait was created in an effort to quantify the trimonoecious trait. The appearance of trimonoecious flowers in watermelon was also reported by Rosa (*Hilgardia* 3:233-250, 1928). Sex expression in watermelon seems to have a high degree of plasticity. Similar to the observations of Rosa (*Hilgardia* 3:233-250, 1928), hermaphroditic flowers sometimes had only one or two stamens, instead of three. Flowers were scored as hermaphroditic if a structure that shed pollen was observed in addition to an ovary and stigma.

The % F flowers in the $F_2$ population ranged from 0 to 30% (FIG. 2b) and the % HM flowers from 0 to 40%. There was a highly significant (P<0.0001) negative correlation (−0.41) between % M and % HM flowers (FIG. 3) as well as between % HM and % F (−0.84) and % HM and % F/P (−0.96) (Table 1). There was a significant positive correlation between % F/P and % Male (0.23), as well as % F/P and % F (0.90). Thus the higher the percentage of male flowers, the lower the percentage of hermaphroditic pistillate flowers.

TABLE 1

Pearson correlations for percent male (% Male), percent female (% Female), percent hermaphrodite (% HM), and percent female of total pistillate (% F/P) flowers in the first twenty flowers of the main vine of the *C. lanatus* var. *lanatus* (ZWRM; PI 593359) x *C. lanatus* var. *citroides* (CTR; PI 244019) $F_2$ population.

|          | % Male   | % Female | % HM     |
|----------|----------|----------|----------|
| % Female | −0.11    |          |          |
| % HM     | −0.41**  | −0.84**  |          |
| % F/P    | 0.23*    | 0.90**   | −0.96**  |

*P < 0.01;
**P < 0.0001

Example 3

QTL Detection

Since the sex expression data were expressed as percentages, the data were arcsine square root transformed before QTL analysis was performed (Sokal and Rohlf, W. H. Freeman and Company, New York, N.Y., 1995; Wills et al., *J Hered* 101:727-736, 2010).

Analysis for the detection of QTL was performed using WinQTL Cartographer (WinQTL Cart) version 2.5 (Wang et al., Windows QTL Cartographer 2.5, Department of Statistics, N.C. State University, Raleigh, N.C., 2011). QTL were identified using composite interval mapping (CIM) (Zeng, *PNAS USA* 90:10972-10976, 1993; Zeng, *Genetics* 136: 1457-1468, 1994) and significance was determined by using permutation tests (1,000 permutations, α=0.05) (Churchill et al., *Genetics* 138:963-971, 1994; Doerge et al., *Genet Mol Biol* 142:285-294, 1996). The standard model (Model 6) with a walk speed of 1 cM was used for CIM analysis.

Figure 3:
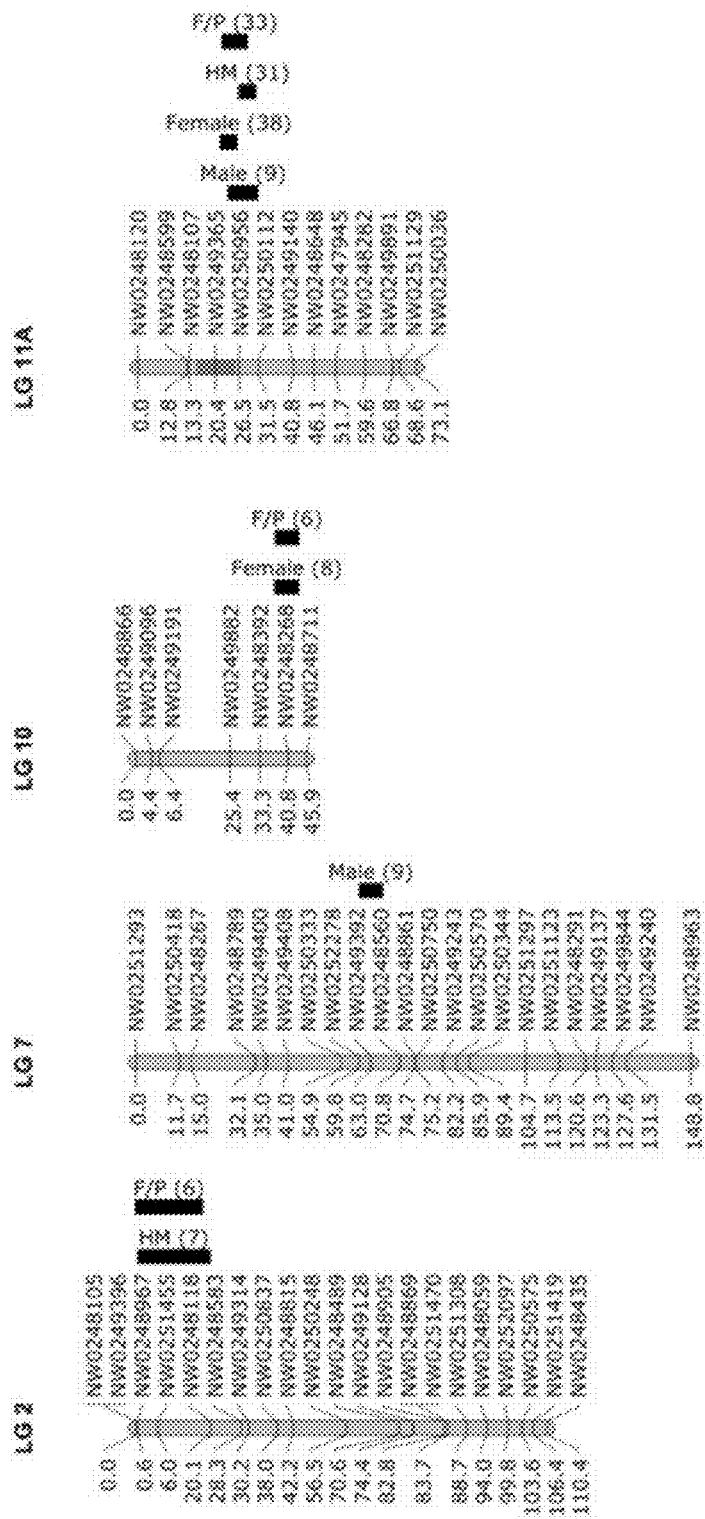
FIG. 3: Shows quantitative trait loci (QTL) identified for the percent male (Male), percent female (Female), percent hermaphrodite (HM) and percent female of pistillate (F/P) flowers in the first twenty flowers of the main vine of the *C. lanatus* var. *lanatus* (ZWRM; PI 593359)×*C. lanatus* var. *citroides* (CTR; PI 244019) $F_2$ population. The length of the bars is equal to the 1-LOD support interval and the number in parentheses is the percentage of phenotypic variation explained by the QTL ($R^2$). The shaded area on LG 11A shows the location of a QTL associated with fruit shape identified previously in the same population.

Results:

Nine QTL associated with sex expression were mapped on four different linkage groups (Table 2, FIG. 3) for the % M, % F, % HM and % F/P traits. These QTL were co-localized at four regions on LGs 2, 7, 10 and 11A. The percentage phenotypic variation explained, ranged from 5.7% (LG 10) to 37.7% (LG11A) and the LOD-1 support interval for the QTL ranged from 4.4 cM (LG 11A) to 19.4 cM (LG 2). Three QTL for % M, % F, % HM and % F/P were co-localized on LG 11A and explained 8.5%, 37.3%, 31.3% and 33.4% of the phenotypic variation for the traits, respectively. A correlation between fruit shape and pistillate vs hermaphroditic flowers in watermelon, cucumber and melon has been reported (Loy, *Cucurbit Genet Coop Rpt* (2005-2006) 28-29:12-13, 2006; Poole et al., *J Agr Res* 71:533-552, 1945; Rosa, *Hilgardia* 3:233-250, 1928). In melon, the a gene, together with the p gene (controlling carpel number) affect fruit shape (Abdelmohsin et al., In: Pitrat, M. (ed.), Cucurbitaceae 2008, Proceedings of the IXth EUCARPIA meeting on genetics and breeding of Cucurbitaceae, INRA, Avignon. France, 2008; Fernandez-Silva et al., *Theor Appl Genet* 121:931-940, 2010; Monforte et al., *Theor Appl Genet* 108:750-758, 2004; Perin et al., *Mol Gen Genom* 266:933-941, 2002). If such a pleiotropic effect is also present in watermelon, one would expect that the a gene would be located in a similar region as QTL controlling fruit shape. Fruit shape index (FSI) data for the population was available from a previous study (Sandlin et al., *Theor Appl Genet* 125(8):1603-18, 2012) and the correlation between FSI and % HM showed a significant correlation (P<0.0001, r=−0.38). A major fruit shape QTL has been reported in the ZWRM×CTR population at 20.4 cM from the top of LG 11A (FIG. 3) and explained 31.8% of the phenotypic variation of this trait (Sandlin et al., *Theor Appl Genet* 125(8):1603-18, 2012). This fruit shape QTL overlaps with the major sex expression QTL identified in the present study (FIG. 3). Thus, the major QTL on LG11A is suggested to be the location of the a gene responsible for andromonoecy in watermelon.

In addition to the co-localized loci on LG11A, three other QTL locations associated with sex expression were identified. Two QTL for % HM and % F were identified on LG 2 and LG 10 and explained 7.3% and 7.7% of phenotypic variation of these traits, respectively. Another QTL was identified on LG7 and explained 9.1% of the phenotypic variation in % M flowers. Therefore it appears that four chromosomal regions are contributing to sex expression in watermelon, with each trait (% HM, % F or % M) being controlled by a major gene (a11.1) and a modifying gene.

genes. The marker (NW0250956) linked to the major QTL on LG 11A is located ~0.6 Mb from Cla011230, homologues (E-value: 0.0) to CsACS2 and CmACS-7 (Boualem et al., *Science* 321:836-838, 2008; Boualem et al., *PLoS ONE* 4:e6144, 2009) on chromosome 3 of the draft watermelon genome sequence (The International Watermelon Genome Initiative, www.iwgi.org; Ren et al., *PLoS ONE* 7:e29453, 2012). Cla011230 also shows high similarity (E-value: 0.0) with the CitACS4 gene previously partially cloned in an individual originating from a cross between *C. colocynthis* and *C. lanatus* var. *lanatus* (Salman-Minkov et al., *Plant Cell Physiol* 49:740-750, 2008). Salman-Minkov et al. (*Plant Cell Physiol* 49:740-750, 2008) reported that CitACS4 transcription was not observed in either floral or vegetative tissues, and suggested that CitACS4 expression might be below the level of detection with the methodology followed, or that the gene was not functional. In order to

TABLE 2

Genomic regions associated with percent male (% Male), percent female (% Female), percent hermaphrodite (% HM), and percent female of total pistillate (% F/P) flowers in the first twenty flowers of the main vine of the *C. lanatus* var. *lanatus* (ZWRM; PI 593359) × *C. lanatus* var. *citroides* (CTR; PI 244019) F$_2$ population.

| Trait | LG$^z$ | Chr$^y$ | Closest marker$^x$ | Position (cM) | LOD | R$^2$ (%) | Additive effect$^v$ | Dominance effect$^v$ | LOD-1 support interval (cM) | LOD-1 support interval (cM) |
|---|---|---|---|---|---|---|---|---|---|---|
| % HM | 2 | 6 | NW0251455 | 11.0 | 3.71 | 7.3 | 0.082 | −0.013 | 0.6 | 20.0 |
| % F/P | 2 | 6 | NW0251455 | 9.0 | 3.77 | 6.3 | −0.233 | −0.066 | 0.0 | 18.0 |
| % Male | 7 | 1 | NW0249392 | 63.3 | 3.80 | 9.1 | 0.016 | −0.038 | 59.9 | 66.2 |
| % Female | 10 | 10 | NW0248268 | 40.8 | 4.76 | 7.7 | 0.077 | −0.008 | 37.3 | 43.8 |
| % F/P | 10 | 10 | NW0248268 | 40.8 | 3.79 | 5.7 | 0.237 | −0.014 | 37.4 | 43.8 |
| % Male | 11A | 3 | NW0250956 | 26.5 | 3.57 | 8.5 | 0.033 | −0.003 | 23.7 | 31.5 |
| % Female | 11A | 3 | NW0250956 | 24.4 | 19.88 | 37.7 | 0.160 | 0.093 | 21.6 | 26.0 |
| % HM | 11A | 3 | NW0250956 | 28.5 | 15.88 | 31.3 | −0.165 | −0.061 | 26.5 | 30.9 |
| % F/P | 11A | 3 | NW0250956 | 24.4 | 18.45 | 33.4 | 0.562 | 0.262 | 22.0 | 28.7 |

$^z$Linkage group as described in Sandlin et al. (*Theor Appl Genet* 125(8): 1603-18, 2012);
$^y$Chromosome of the draft watermelon genome sequence (Ren et al., 2012; The International Watermelon Genome Initiative, www.iwgi.org/);
$^x$Marker sequence information available in Sandlin et al. (*Theor Appl Genet* 125(8): 1603-18, 2012);
$^v$Based on arcsine square root transformed data Example 4

Candidate Genes

BLAST search (Altschul et al., *Nucl Acids Res* 25:3389-3402, 1997) of the draft watermelon genome (The International Watermelon Genome Initiative, www.iwgi.org) was used to determine whether watermelon orthologues of the sex expression genes previously identified in melon or cucumber were located close to the QTL regions identified. The following melon and cucumber sequences were used: F locus [CsACS1 (DQ839410) and CsACS1G (DQ839406)] (Knopf et al., *Plant Cell Physiol* 47:1217-1228, 2006; Trebitsh et al., *Plant Physiol* 113, 1997), M and A loci [CsACS2 (D89732) and CmACS-7 (EU791280 and EU791279)] (Boualem et al., *Science* 321:836-838, 2008; Boualem et al., *PLoS ONE* 4:e6144, 2009) and G locus [CmWIP1 (GQ870274 and GQ870275)] (Martin et al., *Nature* 461:1135-1138, 2009). The same was done for the CitACS1-4 (EF154455, EF154456, EF154457 and EF154458) genes previously identified in watermelon (Salman-Minkov et al., *Plant Cell Physiol* 49:740-750, 2008). The sequences of the SNP markers (Sandlin et al., *Theor Appl Genet* 125(8):1603-18, 2012) closest to the QTL (Table 2) were used to determine the approximate location of the QTL on the draft genome sequence.

Results:

Three of the identified QTL are located on the same watermelon chromosome as sequences homologous to ACS genes. elucidate the potential role of Cla011230 in sex expression in watermelon, we are currently in the process of cloning the entire gene in ZWRM and CTR, the parents of the current mapping population, as well other *C. lanatus* accessions and cultivars.

The CsACS1 and CsACS1G genes (Knopf et al., *Plant Cell Physiol* 47:1217-12282006; Trebitsh et al., *Plant Physiol* 113, 1997) show homology (E-value 0.0) to the Cla014057 gene on chromosome 1 of the draft sequence of watermelon. However, the marker NW0249392, linked to the QTL is ~7.7 Mb away from Cla014057 on chromosome 1. The effect of CsACS1 and CsACS1G on sex expression in cucumber is due to a duplication event (Knopf et al., *Plant Cell Physiol* 47:1217-1228, 2006) and it remains to be seen whether the gene is duplicated in any watermelon cultivars/accessions. Cla014057 shows homology to CitACS2 (Salman-Minkov et al., *Plant Cell Physiol* 49:740-750, 2008), that isolated from an inter-specific cross between *C. colocynthis* and *C. lanatus* var. *lanatus*.

Another ACS homologue (CitACS3) cloned in progeny from the inter-specific *Citrullus* cross by Salman-Minkov et al. (*Plant Cell Physiol* 49:740-750, 2008) is located on chromosome 6 of the draft genome sequence (Cla006634), and ~0.3 Mb from marker NM0251455 (LG 2). CitACS3 gene was expressed in male and hermaphroditic buds, but not in female buds (Salman-Minkov et al., *Plant Cell Physiol* 49:740-750, 2008). The role of ACS genes in sex expression of melon and cucumber makes them prime candidate genes for sex expression in watermelon, as well other cucurbit crops (Boualem et al., *Science* 321:836-838, 2008; Boualem et al., *PLoS ONE* 4:e61444:e6144, 2009; Knopf et al., *Plant Cell Physiol* 47:1217-1228, 2006; Li et al., *Genetics* 182:1381-1385, 2009; Trebitsh et al., *Plant Physiol* 113, 1997).

The location of the ACS genes close to QTL associated with sex expression in watermelon indicates that it is likely that these genes are involved in sex expression. Of note, the role of ethylene in sex expression in watermelon seems to be different from melon and cucumber (where ethylene promotes female flowers), indicating that additional genes may be involved. However, the data strongly indicate that the ACS genes are the most obvious candidate genes for sex expression in watermelon.

While it is known that environmental conditions, including growth of plants in a greenhouse, as well as other factors (e.g. fruit set) play a role in sex expression in watermelon (Grumet et al., In: Wang, Y.-H., Behera, T. K., and Kole, C. (eds.), Genetics, genomics and breeding of cucurbits. Science Publishers, Enfield, N.H., 2012; Robinson et al., Cucurbits. CAB International Publishing, Wallingford, UK, 1997; Rudich et al., *Scientia Hort* 5:339-344, 1976), it remains to be seen whether the QTL reported here will be stable in other populations and environments. However, the co-localization of the major QTL associated with % HM with a fruit shape QTL in watermelon, and a gene with high similarity to the andromonoecious gene identified in other cucurbits support the results reported here.

QTL associated with sex expression in watermelon were identified, including a major QTL (LG11A) that we propose is the location of the a gene responsible for andromonoecy in the species. This research is an important step toward the use of marker assisted selection, as well as the potential cloning of the genes responsible for sex expression in watermelon

What is claimed is:

1. A watermelon plant comprising in its genome at least one introgressed allele locus that confers a percent hermaphroditic flowers phenotype, wherein the locus comprises:
markers NW0248967 (SEQ ID NO:1) and NW0248118 (SEQ ID NO:3) on linkage group 2 (LG2);
or a progeny plant therefrom, wherein said progeny plant comprises said allele locus that confers said percent hermaphroditic flowers phenotype.

2. The watermelon plant of claim 1 wherein the plant is dioecious.

3. The watermelon plant of claim 1 wherein the plant is a tetraploid or a diploid.

4. The watermelon plant of claim 1, wherein said percent hermaphroditic flowers is at least 90%.

5. The watermelon plant of claim 1, wherein the locus comprises:
markers NW0248967 (SEQ ID NO:1) and NW0251455 (SEQ ID NO:11) on LG2;
or
markers NW0248118 (SEQ ID NO:3) and NW0251455 (SEQ ID NO:11) on LG2.

6. A part of the watermelon plant of claim 1, further defined as pollen, an ovule, a leaf, an embryo, a root, a root tip, an anther, a flower, a fruit, a stem, a shoot, a seed, a protoplast, a cell, and a callus.

7. The part of the watermelon plant of claim 6, wherein the part is a seed.

8. A method of detecting in at least one watermelon plant a genotype associated with a desired sex expression phenotype, the method comprising the step of: (i) detecting in at least one watermelon plant an allele of at least one polymorphic nucleic acid that confers a desired sex expression phenotype, wherein the polymorphic nucleic acid comprises:
loci NW0248967 (SEQ ID NO:1) and NW0248118 (SEQ ID NO:3) on linkage group 2 (LG2);
loci NW0252278 (SEQ ID NO:4) and NW0248560 (SEQ ID NO:5) on linkage group 7 (LG7);
loci NW0248392 (SEQ ID NO:6) and NW0248711 (SEQ ID NO:7) on linkage group 10 (LG10); or
loci NW0249365 (SEQ ID NO:8) and NW0250112 (SEQ ID NO:9) on linkage group 11A (LG11A).

9. The method of claim 8, further comprising the step of: (ii) selecting at least one watermelon plant in which a genotype that confers a desired sex expression phenotype has been detected.

10. The method of claim 8, wherein the polymorphic nucleic acid comprises:
loci NW0248967 (SEQ ID NO:1) and NW0251455 (SEQ ID NO:11) on LG2;
loci NW0248118 (SEQ ID NO:3) and NW0251455 (SEQ ID NO:11) on LG2;
loci NW0252278 (SEQ ID NO:4) and NW0249392 (SEQ ID NO:12 on LG7;
loci NW0248560 (SEQ ID NO:5) and NW0249392 (SEQ ID NO:12 on LG7;
loci NW0248392 (SEQ ID NO:6) and NW0248268 (SEQ ID NO:13) on LG10; or
loci NW0248711 (SEQ ID NO:7) and NW0248268 (SEQ ID NO:13) on LG10.

11. A method for producing a watermelon plant that comprises in its genome a locus that confers a percent hermaphroditic flowers phenotype, the method comprising:
(i) crossing a first watermelon plant lacking a locus that confers a percent hermaphroditic flowers phenotype with a second watermelon plant comprising a locus that confers a percent hermaphroditic flowers phenotype, wherein said locus that confers a percent hermaphroditic flowers phenotype comprises:
markers NW0248967 (SEQ ID NO:1) and NW0248118 (SEQ ID NO:3) on linkage group 2 (LG2);
(ii) detecting in progeny resulting from said crossing at least a first marker in or genetically linked to said locus that confers a percent hermaphroditic flowers phenotype; and
(iii) selecting a watermelon plant comprising said marker and said locus that confers a percent hermaphroditic flowers phenotype.

12. The method of claim 11, further comprising the step of:
(iv) crossing the watermelon plant of step (iii) with itself or another watermelon plant to produce a further generation.

13. The method of claim 12, wherein steps (iii) and (iv) are repeated from 3 to 10 times.

14. The method of claim 11, wherein the locus comprises:
markers NW0248967 (SEQ ID NO:1) and NW0251455 (SEQ ID NO:11) on LG2;
or
markers NW0248118 (SEQ ID NO:3) and NW0251455 (SEQ ID NO:11) on LG2.

15. A method of watermelon plant breeding, the method comprising the steps of:
(i) selecting at least a first watermelon plant comprising at least one allele of a polymorphic nucleic acid that comprises a QTL that confers a percent hermaphroditic flowers phenotype, wherein the QTL comprises markers NW0248967 (SEQ ID NO:1) and NW0248118 (SEQ ID NO:3) on LG2; and
(ii) crossing the first watermelon plant with itself or a second watermelon plant to produce progeny watermelon plants comprising the QTL that confers a percent hermaphroditic flowers phenotype.

16. The method of claim 15, wherein the QTL comprises:
markers NW0248967 (SEQ ID NO:1) and NW0251455 (SEQ ID NO:11) on LG2;
or
markers NW0248118 (SEQ ID NO:3) and NW0251455 (SEQ ID NO:11) on LG2.

17. A method of introgressing an allele into a watermelon plant, the method comprising:
(i) genotyping at least one watermelon plant in a population with respect to at least one polymorphic nucleic acid located in or genetically linked to a genomic region that comprises markers NW0248967 (SEQ ID NO:1) and NW0248118 (SEQ ID NO:3) on linkage group 2 (LG2);

(ii) selecting from the population at least one watermelon plant comprising at least one allele that confers a 5 percent hermaphroditic flowers phenotype.

18. The method of claim 17, wherein the polymorphic nucleic acid is located in a genomic region that comprises:

markers NW0248967 (SEQ ID NO:1) and NW0251455 (SEQ ID NO:11) on LG2;

or markers NW0248118 (SEQ ID NO:3) and NW0251455 (SEQ ID NO:11) on LG2.

19. A watermelon plant obtained by the method of claim 17.

* * * * *